United States Patent
Imamura (10) Patent No.: US 9,307,903 B2
(45) Date of Patent: Apr. 12, 2016

(54) IMAGE PROCESSING APPARATUS AND IMAGE PROCESSING METHOD

(71) Applicant: CANON KABUSHIKI KAISHA, Tokyo (JP)

(72) Inventor: Hiroshi Imamura, Kyoto (JP)

(73) Assignee: Canon Kabushiki Kaisha, Tokyo (JP)

( * ) Notice: Subject to any disclaimer, the term of this patent is extended or adjusted under 35 U.S.C. 154(b) by 53 days.

(21) Appl. No.: 14/190,475

(22) Filed: Feb. 26, 2014

(65) Prior Publication Data
US 2014/0240669 A1 Aug. 28, 2014

(30) Foreign Application Priority Data

Feb. 28, 2013 (JP) ................. 2013-040041

(51) Int. Cl.
*A61B 3/14* (2006.01)
*A61B 3/00* (2006.01)
*A61B 3/12* (2006.01)

(52) U.S. Cl.
CPC ............. *A61B 3/1241* (2013.01); *A61B 3/0025* (2013.01)

(58) Field of Classification Search
USPC .................................... 351/200–246
See application file for complete search history.

(56) References Cited

U.S. PATENT DOCUMENTS

| | | | |
|---|---|---|---|
| 4,425,924 A | 1/1984 | Riva et al. | |
| 6,588,901 B1 | 7/2003 | Grinvald et al. | |
| 2006/0147897 A1 | 7/2006 | Grinvald et al. | |
| 2008/0247622 A1* | 10/2008 | Aylward et al. | 382/131 |
| 2008/0312533 A1* | 12/2008 | Balberg et al. | 600/437 |
| 2011/0137157 A1 | 6/2011 | Imamura et al. | |
| 2012/0063660 A1 | 3/2012 | Imamura et al. | |
| 2012/0063663 A1* | 3/2012 | Kawasaki | 382/133 |
| 2012/0130270 A1 | 5/2012 | Imamura et al. | |
| 2012/0194782 A1 | 8/2012 | Imamura | |
| 2012/0218517 A1 | 8/2012 | Imamura | |
| 2013/0058553 A1 | 3/2013 | Yonezawa et al. | |
| 2013/0265543 A1 | 10/2013 | Iwase et al. | |
| 2014/0085606 A1 | 3/2014 | Miyasa et al. | |

FOREIGN PATENT DOCUMENTS

| | | |
|---|---|---|
| EP | 2 455 912 A1 | 5/2012 |
| JP | 2008-104628 A | 5/2008 |

OTHER PUBLICATIONS

Akihito Uji, "Observation of dark tail in diabetic retinopathy uising adaptive optics scanning laser ophthalmoscope", Proceedings of the 66th Annual Congress of Japan Clinical Ophthalmology, 2012, p. 27.

May 22, 2014 European Search Report in European Patent Appln. No. 14156222.3.

* cited by examiner

*Primary Examiner* — Mohammed Hasan
(74) *Attorney, Agent, or Firm* — Fitzpatrick, Cella, Harper & Scinto (57) ABSTRACT

An image processing apparatus obtains a plurality of moving images of a predetermined site of an eye, specifies a vascular region by using at least one moving image of the plurality of moving images, and measures the sizes of blood cell aggregates in a specific vascular branch in the specified vascular region for each moving image of the plurality of moving images.

34 Claims, 9 Drawing Sheets

IMAGE PROCESSING APPARATUS AND IMAGE PROCESSING METHOD

BACKGROUND OF THE INVENTION

1. Field of the Invention

The present invention relates to an image processing apparatus and an image processing method used for ophthalmological consultations.

2. Description of the Related Art

Ophthalmic examinations are widely performed for the purpose of early diagnosis of lifestyle-related diseases and diseases that rank highly among causes of loss of eyesight. A scanning laser ophthalmoscope (SLO), which is an image processing apparatus that uses the principle of a confocal laser microscope, is an apparatus that performs Raster scanning of an eye fundus using a laser that is a measuring beam and obtains a planar image at a high resolution and a high speed based on the intensity of the return light. The apparatus that captures this planar image will be referred to as an SLO apparatus, and the planar image will be referred to as an SLO image below.

In recent years, it has been possible to obtain a retinal SLO image with an improved horizontal resolution by increasing the diameter of the measuring beam in the SLO apparatus. However, there has been a problem in acquiring a retinal SLO image in that increasing the diameter of the measuring beam is accompanied by a decrease in the S/N ratio and the resolution of the SLO image due to aberrations in the eye of the examination subject.

In order to resolve the above-mentioned problem, an adaptive optics SLO apparatus has been developed that has an adaptive optics system that measures aberrations in the eye of the examination subject in real-time using a wavefront sensor and corrects aberrations of a measuring beam or its return light that occur in the examination subject eye using a wavefront compensation device, thereby enabling the acquisition of an SLO image with a high horizontal resolution.

Figure 6A:
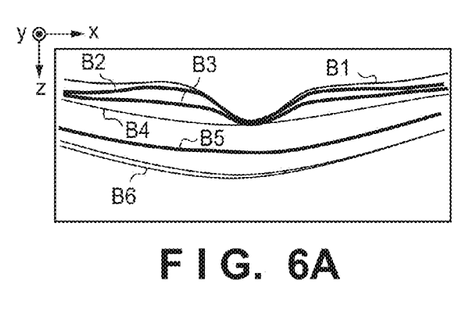
FIGS. 6A to 6G are diagrams for describing images acquired in the embodiment and blood cell dynamics.
Figure 6B:
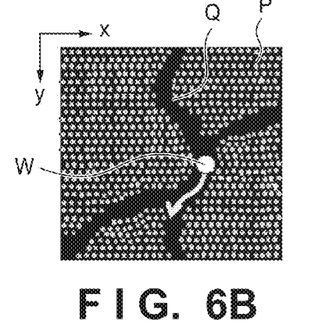

This SLO image having a high horizontal resolution can be acquired as a moving image, and in order to observe blood flow dynamics, for example, in a non-invasive manner, retinal blood vessels are extracted from the frames of the moving image, and the movement speed and the like of blood cells in capillaries are subsequently measured. Also, in order to evaluate the relationship between the photoreceptor cells and the visual function using the SLO image, photoreceptor cells P are detected, and subsequently the density distribution and the alignment of the photoreceptor cells P are measured. FIG. 6B shows an example of an SLO image with a high horizontal resolution. The photoreceptor cells P, a low luminance region Q that corresponds to the position of a capillary, and a high-luminance region W that corresponds to the position of a leukocyte can be observed.

In the case of observing the photoreceptor cells P, measuring the distribution of photoreceptor cells P, or the like using the above-described SLO image, the focus position is set near the retinal outer layer (B5 in FIG. 6A between innermost layer B1 to pigment layer B6) and an SLO image such as FIG. 6B is captured. On the other hand, there are retinal blood vessels and bifurcated capillaries in the retinal inner layers (B2 to B4 in FIG. 6A). 45% of the blood that exists in blood vessels is composed of blood cell components, and of those blood cell components, about 96% are erythrocytes and about 3% are leukocytes. An erythrocyte has a diameter of about 8 µm, and a neutrophil, which is the most common type of leukocyte, is about 12 to 15 µm in size.

Figure 6C:
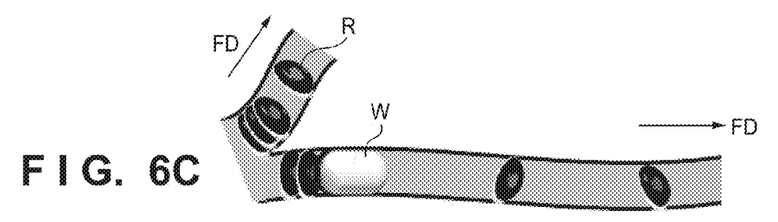
Figure 6D:
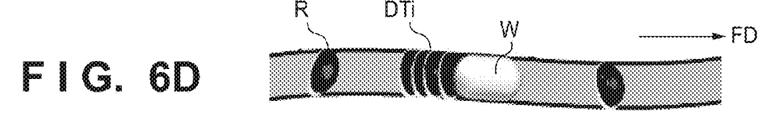
Figure 6E:
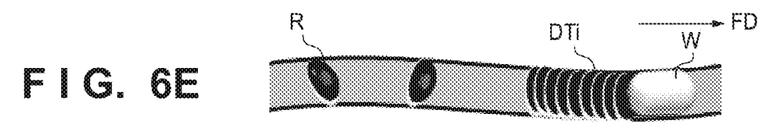
Figure 6F:
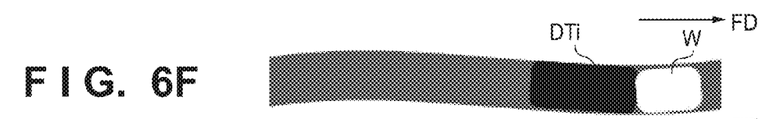

As shown in FIG. 6C, if a leukocyte W is moving in a capillary in flow direction FD, small erythrocytes R flowing in the rear cannot pass the large leukocyte in the front, and therefore erythrocytes accumulate and an aggregation (hereinafter referred to as an "erythrocyte aggregate") forms behind the leukocyte. The size of this kind of erythrocyte aggregate Dti is the smallest immediately subsequent to a vascular bifurcation (FIG. 6C), and it increases gradually as it nears the next vascular bifurcation (FIGS. 6D and 6E). Note that this aggregation occurs physiologically, and if the leukocyte is no longer in front of the erythrocyte aggregate, the erythrocytes will separate and move individually once again. If the focus position is set to the photoreceptor cells and an SLO image having a high horizontal resolution is acquired, the erythrocyte aggregate DTi will be rendered as a dark tail behind the high-luminance leukocyte region W, as shown in FIG. 6F.

Figure 6G:
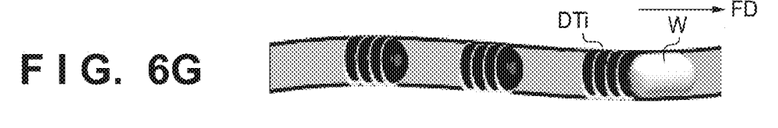

On the other hand, with a diabetic patient for example, erythrocytes will aggregate abnormally and form erythrocyte aggregates DTi regardless of whether or not a leukocyte W is present, as shown in FIG. 6G. In this latter case, erythrocyte aggregates DTi will be present at various positions in the capillary, including the position behind a leukocyte W. Since the erythrocytes are regularly aggregated, the length of the erythrocyte aggregate DTi behind the leukocyte will hardly change when moving between capillary bifurcations. Accordingly, by calculating the change in the size of the erythrocyte aggregate DTi behind the leukocyte based on an SLO moving image with a high horizontal resolution, blood fluidity (the extent to which blood flows smoothly) can be measured in a non-invasive manner.

However, in the case of measuring blood fluidity using multiple SLO images that were captured in the same site in the eye area, there has been a problem in that it is cumbersome to find out the change over time. Also, there has been a problem in that the reliability of measured values is low since statistical values for measured values are measured/calculated without giving consideration to the timing of the heartbeat. Therefore, a technique for (i) quantifying the change over time in measured values for the blood fluidity of the eye area in a simple manner, and (ii) improving the reliability of the measured values for the blood fluidity of the eye area is needed.

Non-Patent Document 1 discloses a conventional technique for non-invasively measuring blood fluidity in which a spatiotemporal image is generated using a capillary branch region in an adaptive optics SLO image and the degree of change in the length of a blood cell aggregate in the spatiotemporal image is measured.

[Non-Patent Document 1] Uji, Akihito, "Observation of dark tail in diabetic retinopathy using adaptive optics scanning laser ophthalmoscope", Proceedings of the 66th Annual Congress of Japan Clinical Ophthalmology, p. 27 (2012).

However, the technique above does not give consideration to simply and accurately obtaining a measurement position that corresponds to a measurement position of an image that was captured in the past in order to easily measure and display the change over time in measured values in images captured at different timings, for example. Also, in the technique above, it is not disclosed that the measured values are more accurately calculated with consideration given to the timing of the heartbeat, for example.

SUMMARY OF THE INVENTION

An embodiment of the present invention discloses an image processing apparatus and an image processing technique for easily and accurately measuring blood fluidity using multiple moving images of a predetermined site.

According to one aspect of the present invention, there is provided an image processing apparatus comprising: an image obtaining unit configured to obtaining a plurality of moving images of a predetermined site in an eye area; a specifying unit configured to specify a vascular region by using at least one moving image of the plurality of moving images; and a measuring unit configured to measure a blood cell aggregate size in a specific vascular branch in the specified vascular region in each moving image of the plurality of moving images.

According to another aspect of the present invention there is provided an image processing method comprising: an image obtaining step of obtaining a plurality of moving images of a predetermined site in an eye area; a specifying step of specifying a vascular region using at least one of the plurality of moving images; and a measuring step of measuring a blood cell aggregate size in a specific vascular branch in the specified vascular region in each of the plurality of moving images.

Further features of the present invention will become apparent from the following description of exemplary embodiments with reference to the attached drawings.

BRIEF DESCRIPTION OF THE DRAWINGS

The accompanying drawings, which are incorporated in and constitute a part of the specification, illustrate embodiments of the invention and, together with the description, serve to explain the principles of the invention.

DESCRIPTION OF THE EMBODIMENTS

Preferred embodiments of the image processing apparatus and method according to the present invention will be described below in accordance with the accompanying drawings. Note that the present invention is not limited to the embodiments disclosed below.

The image processing apparatus according to the present embodiment is configured to measure change in blood cell aggregate sizes in vascular branches (between bifurcations) using the respective SLO images captured at different dates/times and to display the change over time in the measured values from the different dates/times.

Specifically, the image processing apparatus registers multiple SLO moving images that have the same imaging site and were captured at different dates/times. Next, blood vessel extraction is performed on a reference image (described in detail later) and a composite image of blood vessel images is generated. A measurement target vascular branch is specified in the composite image based on the shape of the blood vessels in the parafoveal region. A spatiotemporal image is generated using the vascular branches that were specified in the SLO images that have the same imaging site and were captured at different dates/times, and the change in the size of the blood cell aggregate is measured based on the shape of the path of blood cell aggregates at times at which the phases of pulse signals in the generated spatiotemporal image resemble each other. Furthermore, the measured values are arranged in order of measurement date/time and displayed as a graph with a normal value range attached.

Overall Configuration

Figure 2:
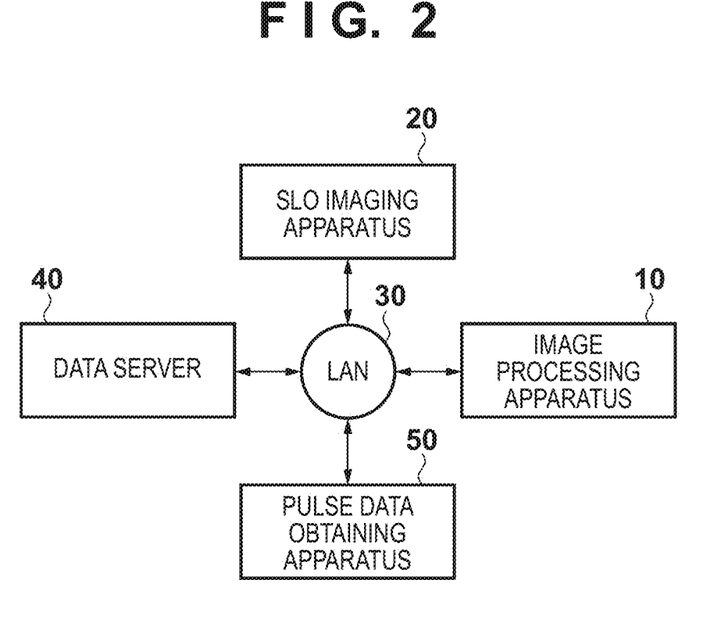
FIG. 2 is a block diagram showing an example of a functional configuration of a system that includes the image processing apparatus according to an embodiment.

FIG. 2 is a diagram showing a configuration of a system that includes an image processing apparatus 10 according to the present embodiment. An image processing apparatus 10 is connected to an SLO imaging apparatus 20 and a data server 40 via a local area network (LAN) 30 that is configured by an optical fiber, a USB, or an IEEE 1394. Note that a configuration is possible in which these devices are connected via an external network such as the Internet, and an alternative configuration is possible in which the image processing apparatus 10 is directly connected to the SLO imaging apparatus 20.

The SLO imaging apparatus 20 is an apparatus that captures an SLO image and transmits information regarding the SLO image and a fixation target position that is used at the time of imaging to the image processing apparatus 10 and the data server 40.

Note that when the SLO images or the fixation target positions are obtained at different magnifications, different imaging positions, or different examination days/times, they are expressed as Dsif (f=1, 2, . . . , n) and Fsif respectively. Here, s is a variable indicating magnification, i is a variable indicating imaging position number, f is a variable indicating examination date/time, and they are written as s=1, 2, . . . , smax, i=1, 2, . . . , imax, and f=1, 2, . . . , fmax respectively. As s increases, the imaging magnification increases (angle of view decreases). Also, the smaller f is, the earlier the examination date/time is.

A pulse data obtaining apparatus 50 is an apparatus that obtains biological signal data (pulse data) that changes autonomically, and it includes a pulse wave meter or an electrocardiograph. The pulse obtaining apparatus 50 obtains data in response to an operation by an operator (not shown) at the same time that the SLO images Dsif are obtained. Here, the pulse data is expressed as a sequence of points having the obtainment time t on one axis and the pulse wave signal value measured by the pulse wave meter on the other axis. The obtained pulse data is transmitted to the image processing apparatus 10 and the data server 40.

The data server 40 holds the SLO images Dsif of the examination subject eye, imaging condition data such as the fixation target positions Fsif that is used at the time of imaging and the pulse data, image characteristics of the eye area, registration parameter values for the positions of the SLO images Dsif, measured values for blood cell aggregate size, normal value range data for the measured values, and the like. Image characteristics for a capillary Q, a blood cell W, and retinal blood vessels are treated as image characteristics of the eye area in the present embodiment. Note that the SLO images Dsif and the fixation target positions Fsif that are used at the time of imaging are output from the SLO imaging apparatus 20. The pulse data is output from the pulse data obtaining apparatus 50. Also, image characteristics of the eye area, registration parameter values for the SLO images Dsif, and measured values regarding the blood cell aggregate size are output from the image processing apparatus 10. Also, in response to a request from the image processing apparatus 10, the data server 40 transmits the SLO images Dsif, the fixation target positions Fsif, the pulse data, the eye area image characteristics, the registration parameter values, the measured values, and the normal value range data for the measured values to the image processing apparatus 10.

Figure 1:
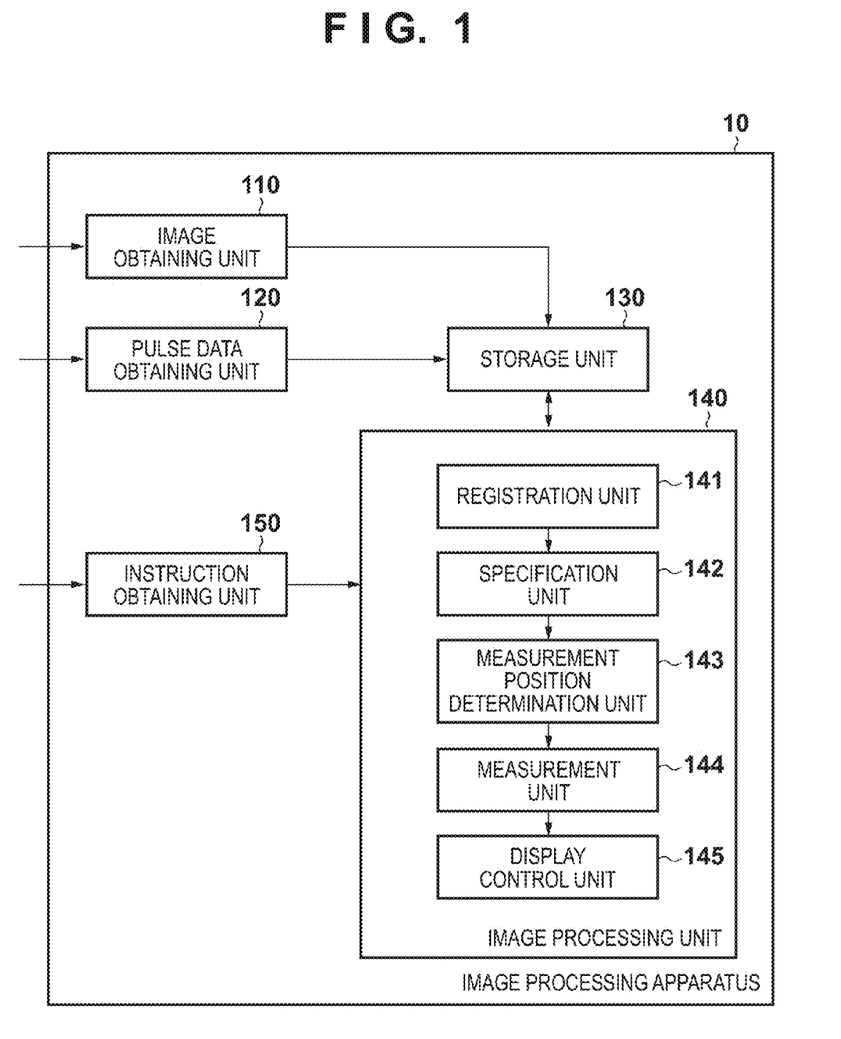
FIG. 1 is a block diagram showing an example of a functional configuration of an image processing apparatus according to an embodiment.

A functional configuration of the image processing apparatus 10 according to the present embodiment will be described next with reference to FIG. 1. FIG. 1 is a block diagram showing an example of a functional configuration of the image processing apparatus 10, and the image processing apparatus 10 has an image obtaining unit 110, a pulse data obtaining unit 120, a storage unit 130, an image processing unit 140, and an instruction obtaining unit 150. Also, the image processing unit 140 includes a registration unit 141, a specification unit 142, a measurement position determination unit 143, a measurement unit 144, and a display control unit 145.

Figure 3:
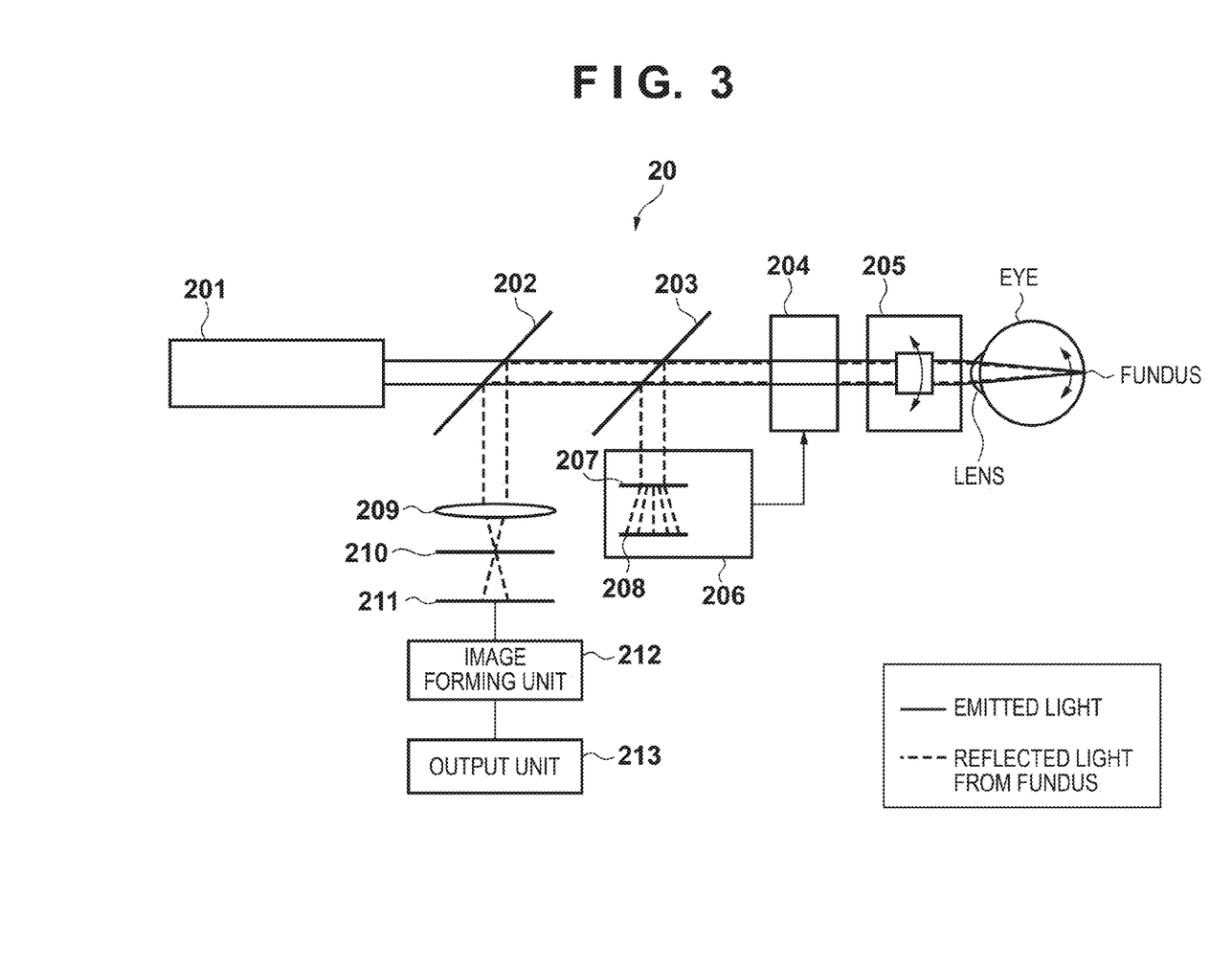
FIG. 3 is a diagram for describing an overall configuration of an SLO imaging apparatus according to the embodiment.

The configuration of an adaptive optics SLO (Adaptive Optics Scanning Laser Ophthalmoscope (AO-SLO)) will be described next with reference to FIG. 3. The AO-SLO 20 has an SLD (Super Luminescent Diode) 201, a Shack-Hartmann wavefront sensor 206, an adaptive optics system 204, beam splitters (202, 203), an X-Y scanning mirror 205, a focus lens 209, an aperture 210, a light sensor 211, an image forming unit 212, and an output unit 213.

Light that is emitted from the SLD 201, which is a light source, is reflected by the eye fundus, a portion of that light is input to the Shack-Hartmann wavefront sensor 206 via the second beam splitter 203, and the rest is input to the light sensor 211 via the first beam splitter 202. The Shack-Hartmann wavefront sensor 206 is a device for measuring eye aberrations and has a lens array 207 and a CCD 208. When incident light passes through the lens array 207, a cluster of light spots appears on the CCD 208, and a wavefront aberration is measured based on the shift in the positions of the projected light spots. The adaptive optics system 204 drives an aberration correction device (a deformable mirror or a space/light phase modulator) based on the wavefront aberration measured by the Shack-Hartmann wavefront sensor 206 and corrects the aberration. The light that has undergone aberration correction is received by the light sensor 211 via the focus lens 209 and the aperture 210. The scanning position on the eye fundus can be controlled by moving the X-Y scanning mirror 205, and data regarding the time (number of frames/frame rate) and the imaging target region that was designated in advance by the operator is obtained. The obtained data is transferred to the image forming unit 212. The image forming unit 212 corrects image deformation caused by variation in scanning speed and luminance values in the transferred data and forms image data (moving image or still image). The output unit 213 outputs the image data formed by the image formation unit 212. In order to set the focus to a specified depth position in the eye fundus, at least one of the following types of adjustment can be used: adjustment using an aberration correction device in the adaptive optics system 204, and adjustment performed by installing a focus adjustment lens (not shown) in the optical system and moving that lens.

Figure 4:
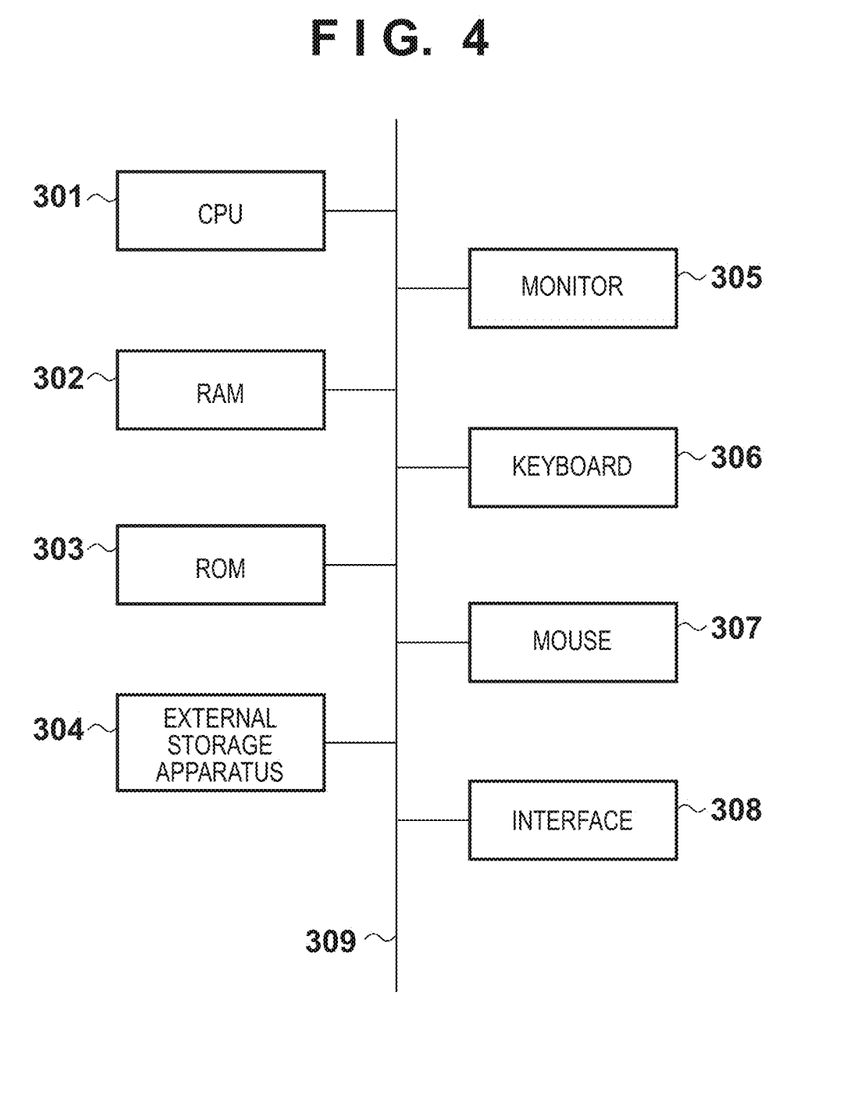
FIG. 4 is a block diagram showing an example of a hardware configuration of an image processing apparatus.

A hardware configuration of the image processing apparatus 10 will be described next with reference to FIG. 4. In FIG. 4, reference numeral 301 is a central processing unit (CPU), reference numeral 302 is a memory (RAM), reference numeral 303 is a control memory (ROM), reference numeral 304 is an external storage apparatus, reference numeral 305 is a monitor, reference numeral 306 is a keyboard, reference numeral 307 is a mouse, and reference numeral 308 is an interface. The external storage apparatus 304 stores a control program for realizing an image processing function according to the present embodiment and data that is used when the control program is executed. The control program and the data are stored in the appropriate RAM 302 via a bus 309, are executed by the CPU 301, and function as the elements of the functional configuration shown in FIG. 1 under the control of the CPU 301.

Figure 5:
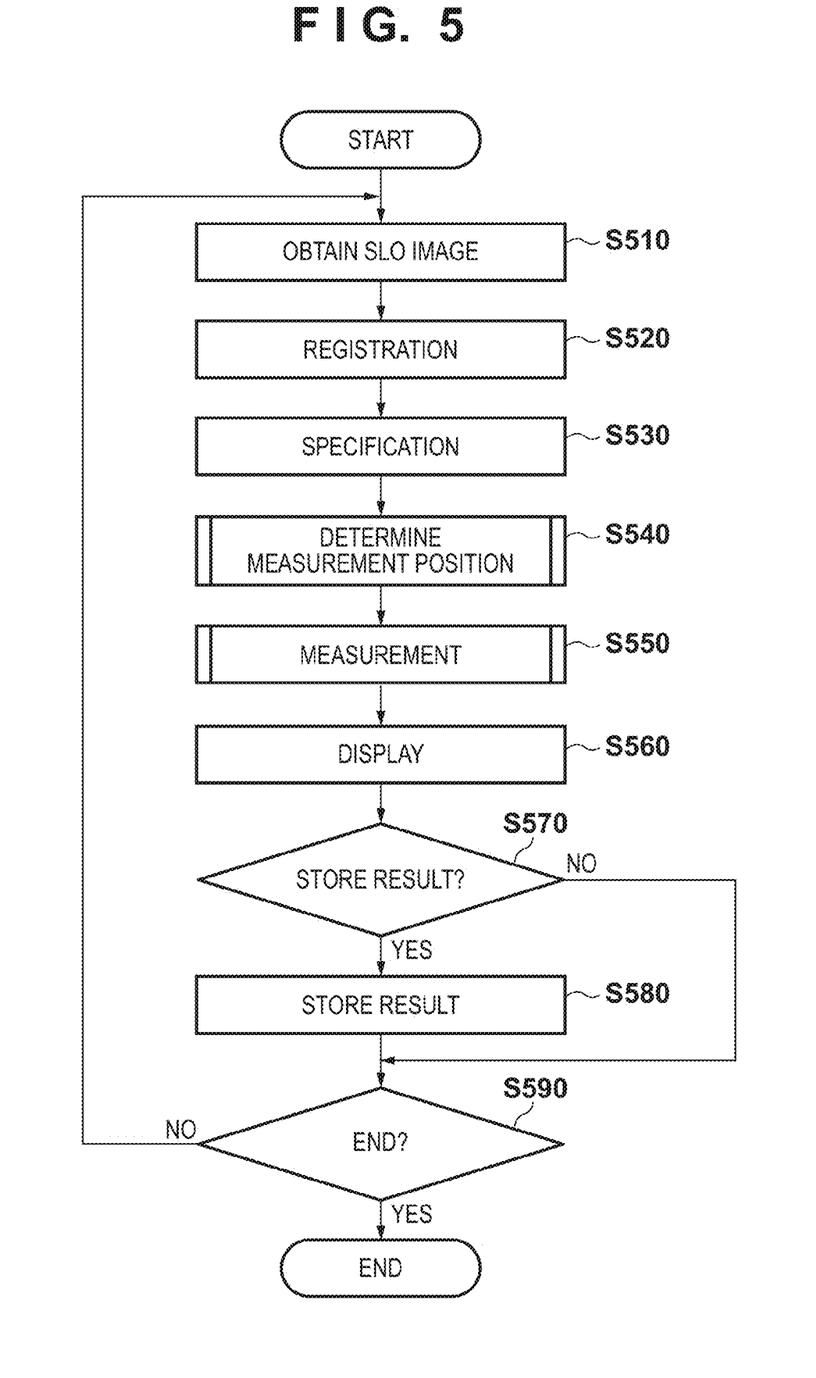
FIG. 5 is a flowchart of processing executed by the image processing apparatus according to the embodiment.

Functions of the blocks that configure the image processing apparatus 10 will be described below in association with a specific execution procedure of the image processing apparatus 10 shown in the flowchart in FIG. 5.

Step S510

The image obtaining unit 110, which is an example of an image obtaining means for obtaining multiple moving images of a predetermined site in an eye area, makes a request to the data server 40 to transfer the past SLO images Dsif (f=1, 2, ..., n−1), the fixation target positions Fsif, and the corresponding pulse data. The data server 40 transfers the data to the image processing unit 10 in response to the request and stores it in the storage unit 130. In the present embodiment, n=6 (i.e., the SLO images Dsi1 to Dsi5 are obtained as the past SLO images).

Next, the image obtaining unit 110 makes a request to the SLO imaging apparatus 20 to obtain the SLO images Dsin and the fixation target positions Fsin that correspond to the latest examination. In the present embodiment, a low-magnification SLO image D1 1n is obtained with the fixation target position F1 1n set to the fovea in the macular region, and high-magnification SLO images D2in are obtained with the fixation target positions F2in set to the foveal and parafoveal regions. Note that the method for setting the imaging position is not limited to this, and a setting of any position may be used. The SLO imaging apparatus 20 obtains and transmits the SLO images D1 1n and D2in and the fixation target positions F1 1n and F2in in response to the obtainment request. The image obtaining unit 110 obtains the information transmitted from the SLO imaging apparatus 20 via the LAN 30 and stores it in the storage unit 130. Note that in the present embodiment, the SLO images D1 1f, D2if, D1 1n, and D2in are moving images whose frames have been registered.

Also, the pulse data obtaining unit 120 makes a request to the pulse data obtaining apparatus 50 to obtain pulse data for biological signals corresponding to Dsin. Here, a pulse wave meter is used as the pulse data obtaining apparatus 50, and pulse wave data is obtained from an earlobe of the examination subject. The pulse data obtaining apparatus 50 obtains the corresponding pulse data and transmits it in response to the acquisition request, and thereby the pulse data obtaining unit 120 receives the pulse data from the pulse data obtaining apparatus 50 via the LAN 30 and stores it in the storage unit 130. Here, consideration will be given to the case where the image obtaining unit 110 starts to obtain the SLO images Din according to the phase of the pulse data obtained by the pulse data obtaining apparatus 50, and the case where the acquisition of the pulse data and the acquisition of the SLO image Dsin are started at the same time immediately subsequent to receiving a request to obtain the SLO images Dsin. In the present embodiment, the acquisition of the pulse data and the SLO images Dsin is started immediately subsequent to receiving a request to obtain the SLO images Dsin.

Step S520

The registration unit 141 registers the SLO images D11f (f=1, 2, ..., n) and the corresponding high-magnification SLO images D2if from the respective examination dates/times and obtains the relative positions of the SLO images D2if on the SLO images D11f. Here, if there is an overlapping region in SLO images D2if from the same examination date/time, the degree of image similarity is first calculated for the overlapping region, and the positions of the SLO images D2if are registered at the position where the degree of image similarity is the greatest. Note that if three or more SLO images with different magnifications are obtained in step S510, registration is performed in sequence starting from the SLO image having the lowest magnification. Also, the registration unit 141 obtains the fixation target positions F2if that were used at the time of capturing the SLO images D2if from the storage unit 130 and uses them as the initial points for searching for the registration parameters in the registration between the SLO images D11f and the SLO images D2if. Any suitable method can be used as the method for image similarity degree and coordinate conversion, and in the present embodiment, registration is performed using a correlation coefficient for the degree of image similarity and Affine conversion as the coordinate conversion method. Composite images of the SLO images D2if are generated using information regarding the relative positions of the SLO images D2if on the SLO images D11f obtained using the registration processing.

Next, registration between the reference image D11r and the SLO images D11f that are not reference images is performed. Here, the examination images (SLO image D11r and SLO images D2ir) that are to be the reference can be selected from among the SLO images from any examination date/time that were obtained in step S510, and in the present embodiment, the SLO image D111 and the SLO images D2i1, or in other words, the SLO images from the earliest examination date/time are used as the reference images.

Furthermore, the relative positions of the SLO images D2if with respect to the reference images D2ir are obtained using the relative position of the reference image D11r with respect to the reference images D2ir, the relative position of the SLO image D11f with respect to the reference image D11r, and the relative positions of the SLO images D2if with respect to the SLO image D11f. Note that the registration of the SLO images D2ir and the SLO images D2if may be performed directly. Here, the registration unit 141 obtains the fixation target positions of the SLO images from the storage unit 130 and uses them as the initial search points in the registration between the SLO images D2if and the SLO image D11f, the registration between the SLO image D11f and the reference image D11r, and the registration between the reference images D11r and D2ir. Any publicly-known method can be used as the registration method, and in the present embodiment, registration is first performed using Affine conversion as a general registration. Next, registration is performed using FFD (Free Form Deformation), which is a non-rigid registration method, as a thorough registration. A correlation coefficient can be used as the degree of image similarity in any registration. Needless to say, the present invention is not limited to this, and any publicly-known degree of image similarity may be used. According to the above description, the pixels of reference images (D11r and D2ir) are associated with the pixels of the SLO images (D11f and D2if) that are not reference images. Note that the present invention is not limited to a registration based on the degree of similarity between pixel values, and, for example, after the specification unit 142 specifies a vascular region, characteristic base registration may be performed using that specified vascular region.

Step S530

The specification unit 142, which is an example of a specifying means for specifying (or identifying) a vascular region in at least one of multiple moving images, specifies a vascular region in the retina using the reference images D2ir. In the present embodiment, the vascular region is specified in the reference images D2ir as the movement range of blood cell components using the following procedure.

(a) Perform subtraction processing between sequential frames of intermediate-magnification images D2ir whose frames have been registered (generate differential moving image).

(b) Calculate luminance value statistic (variance) for the frame direction at the x-y positions of the differential moving image generated in (a).

(c) Specify the region in which the luminance variance is at or above a threshold value Tv at the x-y positions of the differential moving image as the region in which blood cells are moving, or in other words, as the vascular region.

Note that the blood vessel detection processing is not limited to the method above, and any suitable method may be used. For example, in (a) above, division processing for the luminance values between sequential frames may be used (generating a division moving image) instead of using subtraction. Alternatively, a blood vessel may be detected with the application of a filter that enhances linear structures in a specific frame of the SLO image D11r or the SLO images D2ir.

Note that the images obtained by specifying the vascular region out of the SLO images D2ir are denoted below as the blood vessel images V2ir. Also, a composite image is generated by compositing the blood vessel images V2ir using the registration parameter values obtained in step S520.

Step S540

The measurement position determination unit 143 uses the reference image D2ir to automatically determine a vascular branch that is to be the target when measuring the change in the size of a blood cell aggregate. The measurement positions (vascular branches) in the SLO images D2if that are not reference images can be specified according to the positional relationships between the reference images D2ir and the other SLO images D2if. For example, the measurement target vascular branches in the SLO images D2if are determined using the coordinates of the measurement target vascular branches in the reference images D2ir and the relative positions of the reference images D2ir and the SLO images D2if that were obtained in step S520.

Figure 8:
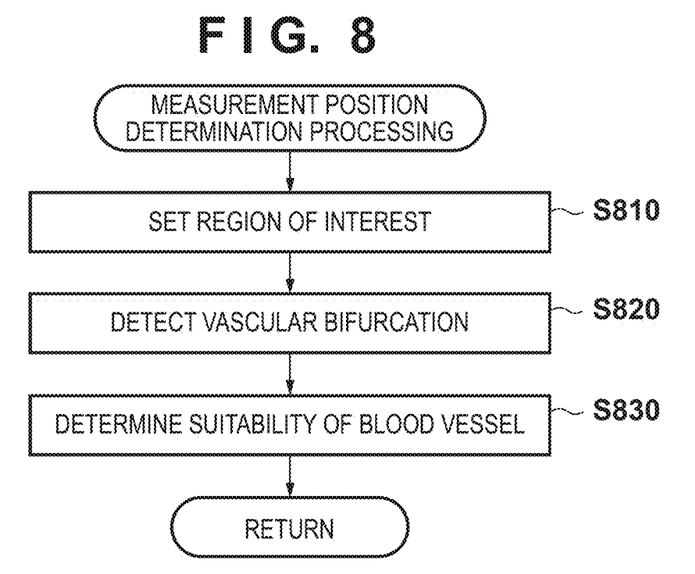
FIG. 8 is a flowchart showing details of measurement position determination processing according to the embodiment.

The processing for determining the measurement positions in the reference images D2ir in the present step will be described in detail later with reference to the flowchart shown in FIG. 8.

Step S550

The measurement unit 144, which is an example of a measuring means, measures the amount of change in the sizes of the blood cell aggregates in the vascular branches (determined in step S540) in the SLO images D2if (f=1, 2, ..., n). Also, using the measured values in the reference image D2ir as the baseline, the measurement unit 144 calculates the differences between the measured values in the SLO images and the baseline. This kind of index is not likely to be influenced by variation caused by sites within a range of normal values or variation caused by individual differences, and therefore the change over time in the measured values can be measured with greater acuity.

Figure 9:
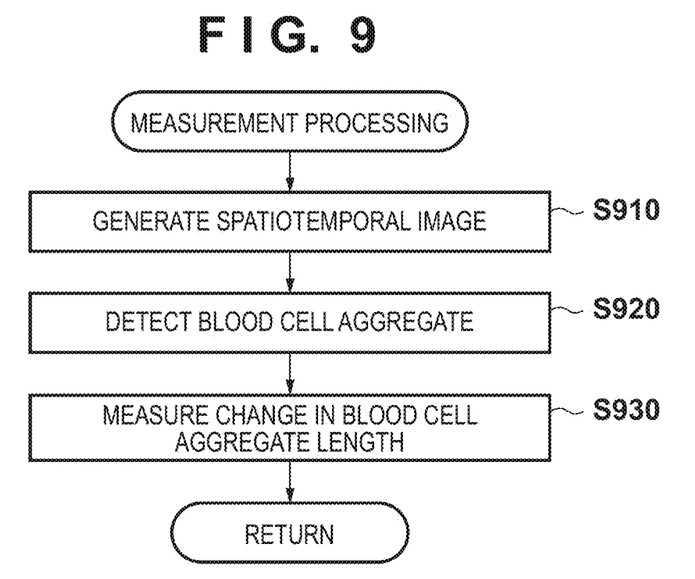
FIG. 9 is a flowchart showing details of measurement processing according to the embodiment.

The processing for measuring the amount of change in the size of the blood cell aggregate in the present step will be described in detail later with reference to the flowchart in FIG. 9.

Step S560

On the monitor 305, the display control unit 145 displays the measured values for the change in the size of the blood cell aggregate with respect to the SLO images D2if obtained in step S550, and a diagram generated based on those measured values.

Figure 10A:
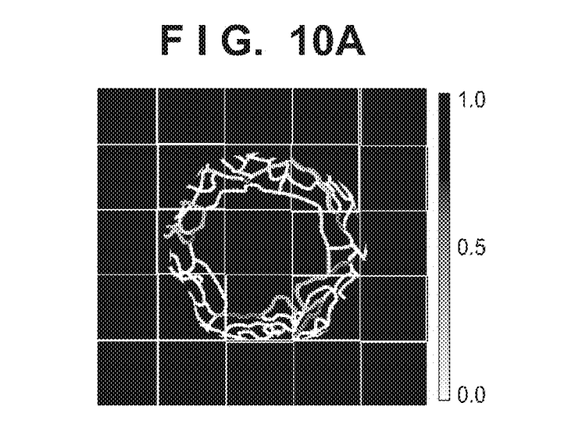
FIGS. 10A to 10C are diagrams for describing display contents regarding values measured in the embodiment.
Figure 10B:
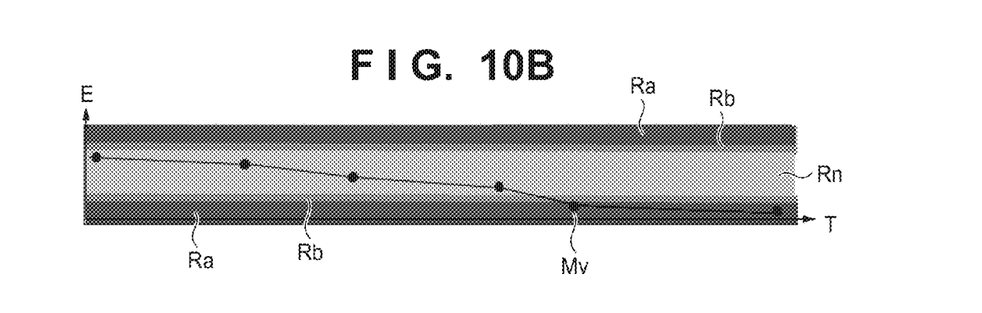

In the present embodiment, the display control unit 145 displays a map and a graph indicating the change over time in the blood cell aggregate sizes as shown in FIG. 10A and FIG. 10B, with respect to the vascular branch designated by the user. In the graph in FIG. 10B, the examination date/time (T) is set on the horizontal axis, the amount of change in the length of the blood cell aggregates (E) is set on the vertical axis, and the measured amounts of change (Mv), a normal value range Rn, a border region for normal values Rb, and an abnormal value region Ra are plotted together. Note that the value of the horizontal axis may indicate the age of the examination subject. This makes it possible instantly to check whether or not there is a problem by comparing the amount of change in the blood cell aggregate size with the range of normal values. Measured values corresponding to an equation (1) that will be described later in step S930 are displayed as the measured values for the change in the blood cell aggregate size. The average value of measured values corresponding to multiple measurement target vascular branches may be used as the plotted measured values (Mv) instead of the average values of measured values corresponding to a single vascular branch designated by the user.

Figure 10C:
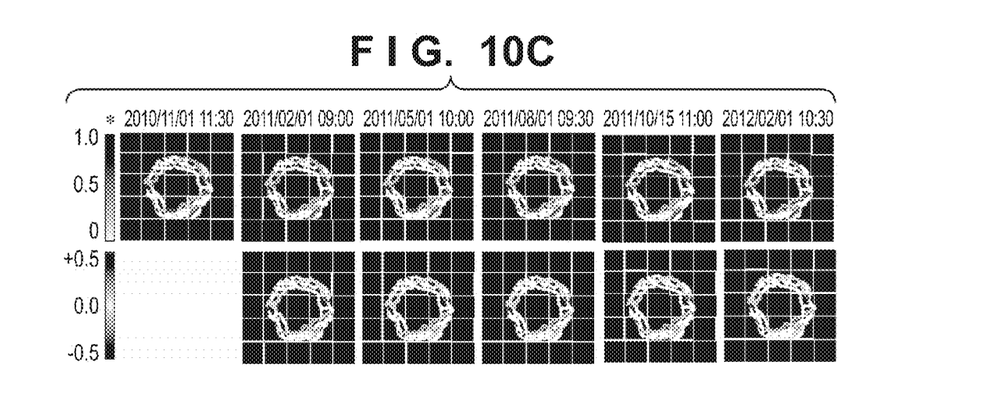

Also, in the present embodiment, maps obtained by coloring the measured values for the change in blood cell aggregate sizes in the measurement target vascular branch in the SLO images D2if (f=1, 2, ..., n) from the respective examination dates/times are arranged in order of examination date/time by the display control unit 145 and displayed as shown in FIG. 10C. According to this, the change over time in the distribution of the blood cell aggregate sizes can be listed and understood. Note that in FIG. 10C, maps of measured values for change in the blood cell aggregate sizes are arranged in the upper row in order of examination date/time, and difference maps with respect to the baseline measured values are in the lower row. The examination dates/times are displayed above the upper row of the measured value maps in FIG. 10C and adding a mark (an asterisk is used in the present example) to the reference examination date/time will facilitate an understanding of which measured value map is the baseline.

Also, the method of displaying the distribution of measured values is not limited to a color display, and for example, it is possible to display them as density values, and they may be included as measured values as well. Furthermore, the measured value is not limited to a value for the change in blood cell aggregate size (e.g., a later-described elongation rate) in the measurement target vascular branches, and for example, deviations from a normal value calculated based on values in a normal value range for the amount of change in the blood cell aggregate size may be displayed as a map, arranged in order of examination date/time, and displayed. Note that the display control in the present invention is not limited to this, and any type of display is possible as long as it is based on the measured values for the blood cell aggregate sizes.

Step S570

The instruction obtaining unit 150 obtains an instruction from the exterior about whether or not to store the SLO images D11f and D2if, the fixation target positions F11f and F2if, pulse wave analysis data, the registration parameter values, the blood vessel images V2if, the measurement target position, and measured values relating to the blood cell aggregate size in the data server 40. This instruction is input by the operator via the keyboard 306 or the mouse 307 for example. If storage is instructed, the procedure moves to the processing of step S580, and if storage is not instructed, the procedure moves to step S590.

Step S580

The image processing unit 140 transmits the examination dates/times, information for identifying the examination subject eye, the SLO images D11f and D2if, the fixation target positions F11f and F2if, pulse wave analysis data, the registration parameters, the blood vessel images V2if, the measurement target positions, and the measured values for the blood cell aggregate size to the data server 40 where they are stored in association with each other.

Step S590

The instruction obtaining unit 150 obtains an instruction from the outside regarding whether or not to end the processing related to the SLO images D2if performed by the image processing apparatus 10. This instruction is input by the operator via the keyboard 306 or the mouse 307. If an instruction to end processing is obtained, the processing ends. On the other hand, if an instruction to continue processing is obtained, the procedure returns to the processing of step S510 and processing for the next examination subject eye (or re-processing for the same examination subject eye) is performed.

The details of the measurement position determination processing executed in step S540 for determining the measurement target vascular branch in the vascular region will be described next with reference to the flowchart shown in FIG. 8.

Step S810

The measurement position determination unit 143 determines a region of interest (ROI) based on the vascular region obtained in step S530. In the present embodiment, an ROI related to the parafovea is set. Specifically, the border of an avascular region is detected in the vascular region obtained in step S530.

Figure 7A:
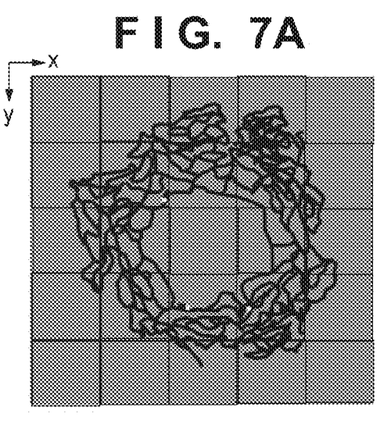
FIGS. 7A to 7F are diagrams for describing image processing contents in the embodiment.
Figure 7B:
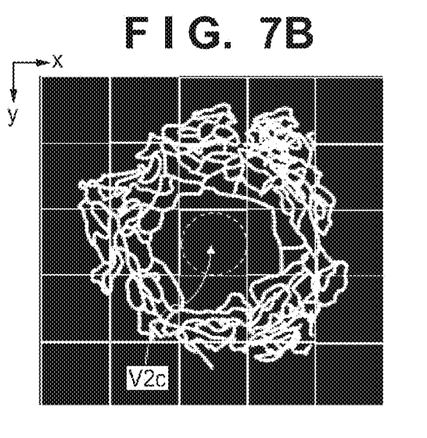

In the vicinity of the retinal fovea, a region in which there are no retinal blood vessels (an avascular region) is present (black, enclosed region in the central portion of FIG. 7A and FIG. 7B). It should be noted that the avascular region near the foveal may be referred to as (Foveal Avascular Zone) FAZ. There is significant individual variation in the shape of the border of the avascular region, and primary lesions in the retinal blood vessels tend to appear in the periphery of the border of the avascular region. Capillaries belonging to the avascular region border are where vascular lesions appear particularly early, and there are cases where the avascular region border is used when determining the position of the fovea. Accordingly, the avascular region border is important as a target of inspection and analysis.

Figure 7C:
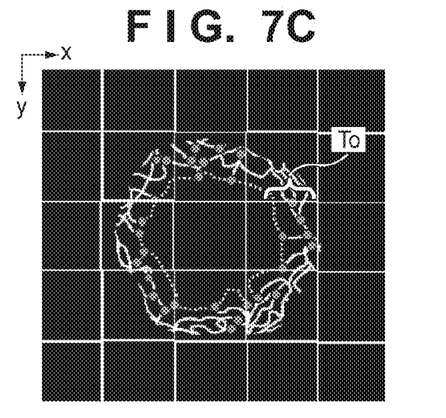

In the present embodiment, in the blood vessel image V2cr (indicated as V2c in FIG. 7B) that is positioned in the center of FIG. 7B, a deformable model (dotted-line portion in same drawing) that corresponds to the inscribed circle in the blood vessel image V2cr is arranged on the composite image for the blood vessel images V2ir. After deformation of the deformable model is complete, its position (dotted line portion in FIG. 7C) indicates the avascular region border. A position on the outer side at a distance of a threshold value To from the avascular region border is determined using a distance image (image that has a distance value from the border in its pixel value) that is obtained by furthermore performing Euclidean distance conversion on the avascular region. Although any value can be set as the threshold value To, it is generally set to around 150 (μm) for a healthy person, and therefore that value will be used in the present embodiment as well. As shown in FIG. 7C, an annular (donut-shaped) region of interest is determined using the two specified borders, namely an inner border and an outer border.

Note that although the width of the annular region that is to be the region of interest was fixed at a threshold value To, the present invention is not limited to this. For example, with a disease such as diabetic retinopathy, where lesions appear in retinal capillaries in the parafovea, capillaries are obstructed as the disease progresses and the avascular region increases in size. Also, if the avascular region increases in size, vascular lesions may possibly occur in a wider range in the periphery of the avascular region. Therefore, a value obtained by multiplying a value that is proportional to the area of the avascular region to the threshold value To may be set as the distance from the avascular region border, and thereby the annular region of interest may be determined.

Step S820

The measurement position determination unit 143 detects bifurcation positions in the vascular region in the region of interest that was set in step S810.

In the present embodiment, the position of a vascular bifurcation needs to be specified in order to measure the change in the size of the blood cell aggregate at a bifurcation such as that shown in FIGS. 6C to 6E. However, due to the fact that there are cases where a blood vessel appears to include a bifurcation when in actuality it is merely an intersection of two blood vessels, the bifurcation areas need to be correctly specified after being distinguished from intersections.

Specifically, thinning processing is performed first on a vascular region in the region of interest and bifurcations are determined based on the continuity of white pixels (pixels whose pixel value is not 0) in the obtained binary image. In the present embodiment, if there are three white pixels among the pixels adjacent to the white pixel that is the determination target, it is determined as a bifurcation, and if there are four white pixels, it is determined as an intersection, and thereby the bifurcation positions as indicated by the round marks in FIG. 7C are determined.

Step S830

Among the blood vessels in the region of interest, the measurement position determination unit 143 determines regions having the bifurcation positions determined in step S820 at both ends as vascular branch candidates in the blood vessel images V2ir. Next, among the vascular branch candidates, a vascular branch candidate that satisfies the following conditions is determined as the measurement target vascular branch:

i) the length of the vascular branch candidate is greater than or equal to the threshold value T1 ii) the diameter (width) of the vascular branch candidate is greater than or equal to a threshold value Tmin and less than a threshold value Tmax.

Here, i) corresponds to the fact that in order for the blood cell aggregate size to change, the blood vessel length needs to be a certain distance. For example, in the case of observing a change in the blood cell aggregate length, with consideration given to the ultimate length of the blood cell aggregate, it is preferable that the blood cell aggregate length is at least 100 μm. Also, ii) is based on the fact that there is a limitation on how small the diameter of the capillary that allows the leukocyte to pass through is, and is furthermore based on a constraint that if the capillary diameter is excessively larger than the size of the leukocyte, erythrocytes will block incident light and the position of the leukocyte cannot be specified. For example, it is preferable that the vascular diameter of the vascular branch is about 10 μm to about 20 μm due to the fact that the erythrocyte diameter is 8 μm and that neutrophils, which are the most common type of leukocyte, are 12 to 15 μm in size.

Note that the method for determining the measurement target vascular branch is not limited to this. For example, the number of measurement target vascular branches may be narrowed down based on at least one of a difference and a variation in luminance values over time in the same moving images of vascular branch candidates. For example, an additional condition for determining a measurement target vascular branch may be used in which a vascular branch that, in the same location throughout all frames calculated in step S530, has a) a variance in luminance values that is greater than or equal to the threshold value Tv, or b) a difference between the largest and smallest luminance values that is greater than or equal to the threshold value Ts is used. This is a condition that is set in order to narrow down the numerous vascular branch candidates to capillary branches that leukocytes and blood cell aggregates pass through. This condition corresponds to the fact that the value of a) or b) above increases in capillaries that the leukocyte and the blood cell aggregate pass through since the luminance is highest at the time of passing of the leukocyte, and the luminance is lowest at the time of passing of the blood cell aggregate.

The details of the measurement processing executed in step S550 will be described next with reference to the flowchart shown in FIG. 9.

Step S910

Figure 7D:
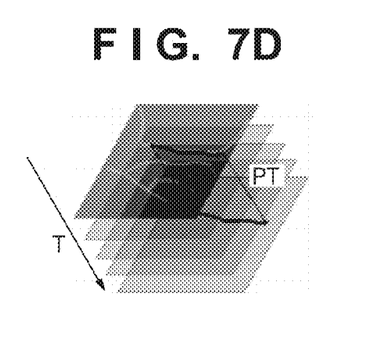
Figure 7E:
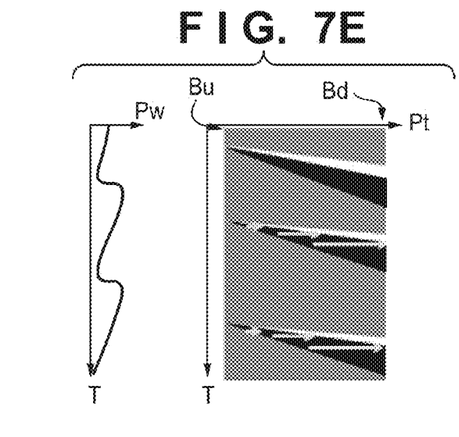
Figure 7F:
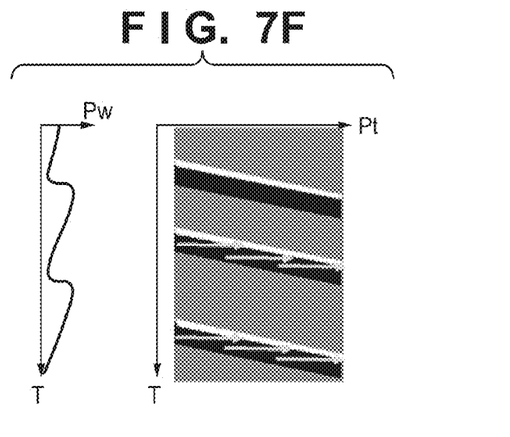

The measurement unit 144 generates a spatiotemporal image such as that shown in FIG. 7E or FIG. 7F with the vascular branch that was determined as the measurement target. The spatiotemporal image includes the position (Pt) in the blood vessel branch on its horizontal axis, the scanning time (T) on its vertical axis, and corresponds to the fact that a curved cross section of the SLO moving image (whose frames have been registered) is generated along the determined blood vessel branch (FIG. 7D). Note that the horizontal axis of the spatiotemporal image is set such that the side that is closer to the origin is the upstream side.

The spatiotemporal image includes a high-luminance linear component that indicates the movement of the leukocyte, and a low-luminance linear component that indicates the movement of the erythrocyte aggregate that is present immediately rearward of the leukocyte.

Step S920

The measurement unit 144 detects a measurement target erythrocyte aggregate in the spatiotemporal image generated in step S910. In the present embodiment, an erythrocyte aggregate that is behind a leukocyte is used as a measurement target, and therefore the movement path of the high-luminance leukocyte is detected first in the spatiotemporal image as shown in FIGS. 7E and 7F, whereafter the low-luminance region directly below the high-luminance path is detected, and thereby the erythrocyte aggregate is specified.

Specifically, line enhancement is performed using any publicly-known line enhancement filter, and the high-luminance leukocyte path is detected by binarizing using a threshold value Tt1. Furthermore, the low-luminance blood cell aggregate path is detected by binarizing the low-luminance region adjacent to the detected high-luminance region using a threshold value Tt2. Note that the method for detecting the blood cell aggregate is not limited to the above-described method, and any publicly-known image processing method may be used.

Next, in order to prevent the blood cell aggregate shape measurement result from being influenced by the heartbeat, only blood cell aggregate paths that correspond to the same phase range in the multiple moving images (SLO images), or in other words, a specific phase section of the pulse data are selected out of the detected blood cell aggregate paths as the measurement target. Here, the measurement unit 144 obtains pulse data corresponding to the SLO moving images D2if in advance from the storage unit 130 and detects the peak values of the pulse data. In the present embodiment, the path from an upstream bifurcation Bu to a downstream bifurcation Bd that is traveled by a blood cell aggregate is used as the measurement target when a pulse data signal Pw is in a specific phase section that is monotonically decreasing. For example, in spatiotemporal images such as FIGS. 7E and 7F, the second and third blood cell aggregate paths respectively are the measurement targets.

Step S930

The measurement unit 144 measures the amount of change in the size of the blood cell aggregate path that was detected and selected in step S920. In the present embodiment, the length (length in the horizontal direction in the spatiotemporal image) in the direction of the central axis of the blood vessel of the erythrocyte aggregate is measured as the erythrocyte aggregate size (length of arrows in FIGS. 7E and 7F), and the elongation rate of the erythrocyte aggregate is calculated according to the following equation.

$$(\text{size of erythrocyte aggregate near downstream bifurcation} - \text{size of erythrocyte aggregate near upstream bifurcation})/(\text{length of vascular branch}) \quad (1)$$

Furthermore, the degree of reliability for the measured value (elongation rate in the present example) is measured based on a statistical value of multiple measured values. In the present embodiment, as an example of the calculation of the degree of reliability, the average value and variance value of the elongation rates of blood cell aggregate paths that were measured in the same spatiotemporal image are obtained, and the average value is the elongation rate of the erythrocyte aggregate at the vascular branch, and the inverse of the calculated variance value is the degree of reliability for the elongation rate in the vascular branch. For example, in spatiotemporal images such as FIGS. 7E and 7F, the elongation rates of the second and third blood cell aggregate paths respectively are measured, the average value and variance value of the measured elongation rates is obtained, and the inverse of the variance value is used as the degree of reliability. Since statistical values are calculated using the elongation rates that were calculated at specific phase sections of the pulse data, it is possible to calculate measured values that are not likely to be influenced by the heartbeat and are more accurate. Note that if the variance value is less than a threshold value Tc, the largest pre-set value for the degree of reliability is used.

Note that the size of the above-described erythrocyte aggregate may be measured using the following method. In other words, the slope (angle) of the erythrocyte aggregate movement path in the spatiotemporal image is calculated using a Hough transformation, and the erythrocyte aggregate movement speed is calculated based on that angle. Next, the erythrocyte aggregate length is measured as:

$$(\text{blood cell aggregate movement speed}) \times (\text{time it takes for blood cell aggregate to pass a certain position in the vascular branch}) \quad (2)$$

That is to say that in the case of observing the movement of the erythrocyte aggregate at a certain position in the vascular branch at a fixed point, it is presumed that the erythrocyte aggregate will pass the observation point at a fixed movement speed (which was calculated based on the slope of the movement path), and thereby the length of the erythrocyte aggregate can be measured by calculating equation (2). This method corresponds to the fact that the length in the vertical direction of the movement path for the erythrocyte aggregate is measured in the spatiotemporal image.

Also, the measured value regarding the change in the blood cell aggregate size is not limited to being calculated/compared using the rate of elongation in the vertical direction or the horizontal direction of the blood cell aggregate in the spatiotemporal image between the vicinity of an upstream bifurcation and the vicinity of a downstream bifurcation. For example, it is possible to calculate a value obtained by determining the difference between lengths of the blood cell aggregate in the vicinity of upstream bifurcations for each point in the vascular branch and integrating them. By calculating this kind of integral value, it is possible to perform a measurement that more accurately reflects fine changes in the blood cell aggregate lengths. Alternatively, the size of the blood cell aggregate may be calculated based on a value measured directly in a frame of the SLO images D2if without the spatiotemporal image being generated. Alternatively, a deviation from a normal value may be calculated based on a value that is within a normal range of values for the elongation rate of the blood cell aggregate size.

According to the above-described configuration, the image processing apparatus 10 automatically determines a vascular branch that is appropriate for measuring the blood cell aggregate size and subsequently measures the amount of change (elongation rate in the present example) in the shape of the blood cell aggregate in the vascular region (between bifurcations) at times when the phases of pulse wave data resemble each other. Furthermore, the image processing apparatus 10 measures the amounts of change in the shape of the blood cell aggregate between the vascular bifurcations in the respective SLO images captured at different dates/times and subsequently displays the change over time in the measured values from the different examination dates/times.

According to this, a measurement target vascular branch is easily specified and thereafter the change over time in blood fluidity at different examination dates/times can be accurately measured and displayed.

Embodiments of the present invention can also be realized by a computer of a system or apparatus that reads out and executes computer executable instructions recorded on a storage medium (e.g., non-transitory computer-readable storage medium) to perform the functions of one or more of the above-described embodiment(s) of the present invention, and by a method performed by the computer of the system or apparatus by, for example, reading out and executing the computer executable instructions from the storage medium to perform the functions of one or more of the above-described embodiment(s). The computer may comprise one or more of a central processing unit (CPU), micro processing unit (MPU), or other circuitry, and may include a network of separate computers or separate computer processors. The computer executable instructions may be provided to the computer, for example, from a network or the storage medium. The storage medium may include, for example, one or more of a hard disk, a random-access memory (RAM), a read only memory (ROM), a storage of distributed computing systems, an optical disk (such as a compact disc (CD), digital versatile disc (DVD), or Blu-ray Disc (BD)™), a flash memory device, a memory card, and the like.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

The above-described processing method can be applied to a portion other than a retina. For example, the above-described processing method can be applied to an anterior eye part.

This application claims the benefit of Japanese Patent Application No. 2013-040041, filed Feb. 28, 2013, which is hereby incorporated by reference herein in its entirety.

What is claimed is:

1. An image processing apparatus comprising:
    an image obtaining unit configured to obtain a plurality of moving images of a predetermined site in an eye area;
    a specifying unit configured to specify a vascular region by using at least one moving image of the plurality of moving images; and
    a measuring unit configured to measure a blood cell aggregate size in a specific vascular branch in the specified vascular region in each moving image of the plurality of moving images.

2. The apparatus according to claim 1, wherein the measuring unit measures a change over time in measured values based on the blood cell aggregate size in each of the plurality of moving images.

3. The apparatus according to claim 2, further comprising:
    a display control unit configured to display the change over time measured in the plurality of moving images by the measuring unit.

4. The apparatus according to claim 1, wherein the measuring unit outputs a plurality of measured values based on the blood cell aggregate size measured in the same phase range in a heartbeat or pulse wave data for each of the plurality of moving images.

5. The apparatus according to claim 4, further comprising:
    a calculating unit configured to calculate a measured value reliability degree based on a statistical value for the plurality of measured values.

6. The apparatus according to claim 1, further comprising:
    a measurement position determining unit configured to determine a measurement target vascular branch based on the vascular bifurcations in the vascular region specified by the specifying unit.

7. The apparatus according to claim 6, wherein the measurement position determining unit uses a region having detected vascular bifurcations at both ends in the vascular region as a vascular branch candidate and determines a measurement target vascular branch out of the vascular branch candidates based on the vascular length and diameter.

8. The apparatus according to claim 7, wherein the measurement position determining unit furthermore determines the measurement target vascular branch based on at least one of the difference between, and the variance in, luminance values over time in the moving images of the vascular branch candidates.

9. The apparatus according to claim 6, wherein the measurement position determining unit determines the measurement target vascular branch in the vascular region specified by the specifying unit for one moving image out of the plurality of moving images, and determines a measurement target vascular branch in another moving image based on the positional relationship between the one moving image and the other moving image.

10. The apparatus according to claim 1, wherein the image obtaining unit obtains the plurality of moving images by imaging the same area of the eye at different times.

11. An image processing method comprising:
    an image obtaining step of obtaining a plurality of moving images of a predetermined site in an eye area;
    a specifying step of specifying a vascular region using at least one moving image of the plurality of moving images; and
    a measuring step of measuring a blood cell aggregate size in a specific vascular branch in the specified vascular region in each of the plurality of moving images.

12. The method according to claim 11, wherein in the measuring step, change over time in measured values based on the blood cell aggregate size in each of the plurality of moving images is measured.

13. The method according to claim 12, further comprising:
    a display control step of displaying the change over time measured in the plurality of moving images by the measuring means.

14. The method according to claim 11, wherein in the measuring step, a plurality of measured values based on the blood cell aggregate size measured in the same phase range in a heartbeat or pulse wave data for each of the plurality of moving images are output.

15. The method according to claim 14, further comprising:
    a calculating step of calculating a measured value reliability degree based on a statistical value for the plurality of measured values.

16. The method according to claim 11, further comprising:
    a measurement position determining step of determining a measurement target vascular branch based on the vascular bifurcations in the vascular region specified in the specifying step.

17. The method according to claim 16, wherein in the measurement position determining step, a region having detected vascular bifurcations at both ends in the vascular region is used as a vascular branch candidate and a measurement target vascular branch is determined out of the vascular branch candidates based on the vascular length and diameter.

18. The method according to claim 17, wherein in the measurement position determining step, the measurement target vascular branch is furthermore determined based on at least one of the difference between, and the variance in, luminance values over time in the moving images of the vascular branch candidates.

19. The method according to claim 16, wherein in the measurement position determining step, the measurement target vascular branch is determined in the vascular region specified in the specifying step for one moving image out of the plurality of moving images, and a measurement target vascular branch in another moving image is determined based on the positional relationship between the one moving image and the other moving image.

20. The method according to claim 11, wherein, in the image obtaining step, the plurality of moving images are obtained by imaging the same area of the eye at different times are obtained.

21. A non-transitory computer readable storage medium storing a program for causing a computer to execute an image processing method, the method comprising:
    an image obtaining step of obtaining a plurality of moving images of a predetermined site in an eye area;

a specifying step of specifying a vascular region using at least one moving image of the plurality of moving images; and a measuring step of measuring a blood cell aggregate size in a specific vascular branch in the specified vascular region in each of the plurality of moving images.

22. An image processing apparatus comprising:
an image obtaining unit configured to obtain a moving image of an eye area;
a specifying unit configured to specify a vascular region by using the moving image; and
a determining unit configured to determine a vascular branch based on the vascular bifurcations in the specified vascular region.

23. The apparatus according to claim 22, further comprising:
a measuring unit configured to measure a blood cell aggregate size in the determined vascular branch in the moving image.

24. The apparatus according to claim 22, wherein the determining unit uses a region having detected vascular bifurcations at both ends in the vascular region as a vascular branch candidate and determines the vascular branch out of the vascular branch candidates based on the vascular length and diameter.

25. The apparatus according to claim 24, wherein the determining unit furthermore determines the vascular branch based on at least one of the difference between, and the variance in, luminance values over time in the moving image of the vascular branch candidates.

26. The apparatus according to claim 22, wherein the determining unit determines the vascular branch in the vascular region specified by the specifying unit for one moving image out of a plurality of moving images, and determines a vascular branch in another moving image based on the positional relationship between the one moving image and the other moving image.

27. The apparatus according to claim 26, wherein the image obtaining unit obtains the moving image by imaging the same area of the eye at different times.

28. An image processing method comprising:
an image obtaining step of obtaining a moving image of an eye area;
a specifying step of specifying a vascular region using the moving image; and
a determining step of determining a vascular branch based on the vascular bifurcations in the specified vascular region.

29. The method according to claim 28, further comprising:
a measuring step of measuring a blood cell aggregate size in the determined vascular branch in the moving image.

30. The method according to claim 28, wherein in the determining step, a region having detected vascular bifurcations at both ends in the vascular region is used as a vascular branch candidate and the vascular branch is determined out of the vascular branch candidates based on the vascular length and diameter.

31. The method according to claim 30, wherein in the measurement position determining step, the measurement target vascular branch is furthermore determined based on at least one of the difference between, and the variance in, luminance values over time in the moving image of the vascular branch candidates.

32. The method according to claim 28, wherein in the determining step, the vascular branch is determined in the vascular region specified in the specifying step for one moving image out of a plurality of moving images, and a vascular branch in another moving image is determined based on the positional relationship between the one moving image and the other moving image.

33. The method according to claim 32, wherein, in the image obtaining step, the moving image is obtained by imaging the same area of the eye at different times.

34. A non-transitory computer-readable storage medium storing a program for causing a computer to execute an image processing method, the method comprising:
an image obtaining step of obtaining a moving images of an eye area;
a specifying step of specifying a vascular region using the moving image; and
a determining step of determining a vascular branch based on the vascular bifurcations in the specified vascular region.

* * * * *